United States Patent [19]

Fischer et al.

[11] Patent Number: 4,480,105
[45] Date of Patent: Oct. 30, 1984

[54] 3,5-DISUBSTITUTED PHTHALIC ACIDS AND PHTHALIC ANHYDRIDES

[75] Inventors: Walter Fischer; Vratislav Kvita, both of Reinach; Hans Zweifel, Basel, all of Switzerland

[73] Assignee: Ciba-Geigy Corporation, Ardsley, N.Y.

[21] Appl. No.: 373,573

[22] Filed: Apr. 30, 1982

Related U.S. Application Data

[62] Division of Ser. No. 258,268, Apr. 28, 1981, Pat. No. 4,363,917.

[30] Foreign Application Priority Data

May 6, 1980 [CH]  Switzerland ............... 3518/80

[51] Int. Cl.³ .......................................... C07D 307/89
[52] U.S. Cl. ................................ 549/243; 548/476; 548/480; 562/432
[58] Field of Search .......................................... 549/243

[56] References Cited

U.S. PATENT DOCUMENTS 3,520,890  7/1970  Fouche ............................. 549/243
3,850,965  11/1974  Williams ........................... 549/243
3,857,861  12/1974  Lang ................................. 549/243
4,363,917  12/1982  Fischer et al. ................... 548/480

FOREIGN PATENT DOCUMENTS 1571742  7/1980  United Kingdom .

Primary Examiner—Alton D. Rollins
Assistant Examiner—James H. Turnipseed
Attorney, Agent, or Firm—Michael W. Glynn

[57] ABSTRACT

Novel compounds of the formula II

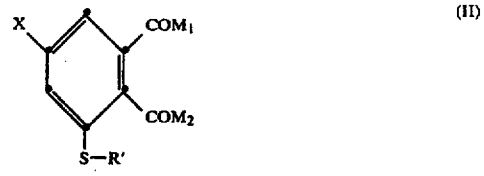

are described, in which $M_1$ and $M_2$ individually are —OH or together are —O—, X is —NO$_2$, —OR', —SR' or SO$_2$R' and the (R')s independently of one another are $C_{1-20}$-alkyl, $C_{3-5}$-alkenyl, $C_{3-5}$-alkynyl, $C_{2-4}$-monohydroxyalkyl, $C_{1-12}$-halogenoalkyl, benzyl, $C_{5-12}$-cycloalkyl, phenyl, carboxyphenyl, halogenophenyl, nitrophenyl, alkyl- or alkoxy-phenyl each having 1–4 C atoms in the alkyl or alkoxy moieties, or acetylaminophenyl, such as for example 3-n-butylthio-5-nitrophthalic anhydride. The compounds (II) in which $M_1$ and $M_2$ together are —O— are suitable as sensitizers for photocrosslinkable polymers or as initiators for the photopolymerization of ethylenically unsaturated compounds or for the photochemical crosslinking of polyolefins, and those where $M_1$ and $M_2$ are —OH are useful intermediates for those wherein $M_1$ and $M_2$ together are —O—.

4 Claims, No Drawings

3,5-DISUBSTITUTED PHTHALIC ACIDS AND PHTHALIC ANHYDRIDES

This is a division of application Ser. No. 258,268, filed on Apr. 28, 1981, now U.S. Pat. No. 4,363,917.

The present invention realtes to novel 3,5-disubstituted phthalimides, phthalic acids and phthalic anhydrides, processes for their preparation and the use of the novel 3,5-disubstituted phthalimides and phthalic anhydrides as sensitisers for photocrosslinkable polymers or, preferably mixed with amines, as initiators for the photopolymerisation of ethylenically unsaturated compounds or for the photochemical crosslinking of polyolefins.

Thioxanthones which are unsubstituted or substituted by halogen, especially by chlorine, are amongst the best known and most active sensitisers for photo-induced crosslinking reactions. The prerequisite for a successful application of this type is a good compatibility of the sensitiser with the polymer, i.e. the sensitiser must be miscible with the polymer up to high concentrations. Furthermore, the sensitisers must be readily soluble in the solvents used in the processing of the polymers. The abovementioned thioxanthones do not satisfy these requirements in every respect; in particular, they easily demix in the polymer, as a result of which their sensitising action is greatly impaired.

It is also known that the photopolymerisation of ethylenically unsaturated compounds can be initiated by aromatic ketones of the benzophenone, anthraquinone, xanthone and thioxanthone type. Furthermore, it is known from U.S. Pat. No. 3,759,807 that the initiating action of these aromatic ketones can be accelerated by the addition of organic amines. Though these amines do not usually possess an initiating action by themselves, they act in combination with aromatic ketones as activators or accelerators. This is of great importance industrially because the production rate of photochemically cured coatings or printing inks primarily depends on the polymerisation rate of the unsaturated compound.

Novel phthalimides, phthalic acids and phthalic anhydrides of the formula I or II

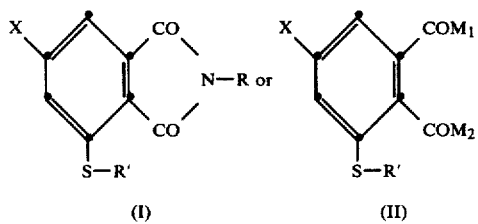

have now been found, in which $M_1$ and $M_2$ individually are —OH or together are —O—, R is hydrogen, $C_{1-20}$-alkyl, $C_{2-5}$-alkenyl, $C_{3-5}$-alkynyl, $C_{5-12}$-cycloalkyl, benzyl, phenyl or toluyl, X is —NO$_2$, —OR', —SR' or —SO$_2$R' and the (R')s independently of one another are $C_{1-20}$-alkyl, $C_{3-5}$-alkenyl, $C_{3-5}$-alkynyl, $C_{2-4}$-monhydroxyalkyl, $C_{1-12}$-halogenoalkyl, benzyl, $C_{5-12}$-cycloalkyl, phenyl, carboxyphenyl, halogenophenyl, nitrophenyl, alkyl- or alkoxyphenyl each having 1–4C atoms in the alkyl- or alkoxymoieties, or acetylaminophenyl.

The phthalimides of the formula I and the phthalic anhydrides of the formula II ($M_1$ and $M_2$ together=—O—) are outstandingly suitable for use as sensitisers for photocrosslinkable polymers. They are distinguished in particular by a good compatibility with the polymer, a good solubility in customary organic solvents and a high photosensitivity. Moreover, the UV absorption can be influenced in such a way that the phthalimides and phthalic anhydrides according to the invention also have a sensitising action on irradiation with UV light of long wavelength (up to about 450 nm) and thus effect the crosslinking of the photosensitive polymers. Photosensitising phthalimides and phthalic anhydrides having donors in the 3-position were not known hitherto.

The phthalimides and phthalic anhydrides according to the invention are also suitable, preferably mixed with organic amines, an initiators for the photopolymerisation of ethylenically unsaturated compounds or for the photochemical crosslinking of polyolefins.

Alkyl, monohydroxyalkyl, halogenoalkyl, alkenyl and alkynyl groups R or R' of the type defined can be straight-chain or branched. Halogenoalkyl groups R' can be substituted by one or more halogen atoms, such as chlorine or bromine and especially fluorine. Examples of alkyl, monohydroxyalkyl, halogenoalkyl, alkenyl and alkynyl groups R or R' of the type defined are methyl, ethyl, n-propyl, isopropyl, n-, sec.- and tert.-butyl, n-pentyl, 2- or 3-pentyl, n-hexyl, n-heptyl, 3-heptyl, n-octyl, n-decyl, n-dodecyl, n-tridecyl, n-tetradecyl, n-hexadecyl, n-octadecyl and eicosyl; 2-hydroxyethyl, 2- and 3-hydroxypropyl and 3- and 4-hydroxybutyl; trifluoromethyl, 2-chloroethyl, 2-bromoethyl, 2,2,2-trifluoroethyl, —CH$_2$CH$_2$C$_4$F$_9$, —CH$_2$CH$_2$C$_6$F$_{13}$ and —CH$_2$CH$_2$C$_8$F$_{17}$; vinyl, allyl, methallyl, 2-butenyl and 4-pentenyl; and 2propynyl, 3-butynyl and 4-pentynyl.

Alkyl groups R are preferably straight-chain and have especially 1–10 and in particular 1–6 C atoms. Methyl is very particularly preferred. Preferred alkenyl and alkynyl groups R or R' are vinyl (R), allyl, methallyl, 2-butenyl and propynyl. Alkyl groups R' preferably have 1–10 C atoms. Straight-chain alkyl groups R' having 1–10 and especially 1–4 C atoms are particularly preferred.

Halogenoalkyl groups R' are likewise preferably straight-chain and have 1–10 C atoms. Trifluoromethyl, —CH$_2$CF$_3$ and —CH$_2$CH$_2$C$_n$F$_{2n+1}$ in which n=4, 6 or 8 are particularly preferred.

Examples of cycloalkyl groups R and R' are cyclopentyl, cyclohexyl, cyclooctyl and cyclododecyl. Cyclohexyl is preferred. A particularly suitable toluyl group R is p-toluyl.

Carboxyphenyl, halogenophenyl, nitrophenyl, alkylphenyl and alkoxyphenyl groups R' can be monosubstituted or polysubstituted. Phenyl groups having one or two of the said substituents are preferred. Examples of suitable halogen atoms are fluorine, bromine and especially chlorine. Examples of groups of this type are 2-carboxyphenyl; 3-chloro- or 3-bromo-phenyl, 3,4-dichlorophenyl, 2,5-dichlorophenyl, 3,4-dibromophenyl and 4-chloro-, 4-bromo- or 4-fluoro-phenyl; 3- or 4-nitrophenyl and 3,5-dinitrophenyl; o-, m- and p-toluyl, 3,4-dimethylphenyl, 4-ethylphenyl and 4-n-butylphenyl; and 2-, 3- or 4-methoxyphenyl, 3- and 4-ethoxyphenyl, 2,5-dimethoxyphenyl, 3,4-diethoxyphenyl, 4-n-propoxyphenyl, 4-isopropoxyphenyl and 4-n-butoxyphenyl. Preferred carboxyphenyl, halogenophenyl, alkylphenyl and alkoxyphenyl groups R' are 2-carboxyphenyl, 3,4-dichlorophenyl, p-toluyl and 4-methoxyphenyl.

Preferred compounds of the formula I or II are those in which $M_1$ and $M_2$ together are —O—, R is hydrogen, $C_{1-6}$-alkyl, phenyl or p-toluyl, X is $-NO_2$, $-Oalkyl$ having 1-4 C atoms, especially methoxy, $-SO_2$-phenyl or $-SR'$ and the (R')s independently of one another are $C_{1-10}$-alkyl, $C_{1-10}$-halogenoalkyl, phenyl, p-methoxyphenyl, p-toluyl, 2-carboxyphenyl or 3,4-dichlorophenyl, and particularly preferred compounds of the formulae I and II are those in which $M_1$ and $M_2$ together are $-O-$, R is hydrogen, $C_{1-6}$-alkyl, phenyl or p-toluyl, X is $-NO_2$, $-SO_2$-phenyl, $-S$-phenyl, $-S-C_{1-10}$-alkyl or $-S-C_{1-10}$-halogenoalkyl and R' is $C_{1-10}$-alkyl, $C_{1-10}$-halogenoalkyl, phenyl, p-methoxyphenyl, p-toluyl, 2-carboxyphenyl or 3,4-dichlorophenyl.

The compounds of the formula I which are particularly preferred are those in which R is hydrogen or $C_{1-6}$-alkyl, X is $-NO_2$, $-SO_2$-phenyl or $-SR'$ and the (R')s independently of one another are $C_{1-10}$-alkyl or phenyl, and especially those in which R is hydrogen or methyl, X is $-NO_2$ or $-SR'$ and the (R')s independently of one another are $C_{1-10}$-n-alkyl or phenyl.

Compounds of the formulae I and II which are very particularly preferred are those in which $M_1$ and $M_2$ together are $-O-$, R is hydrogen or methyl, X is $-NO_2$ and R' is $C_{1-10}$-n-alkyl or phenyl.

The compounds of the formulae I and II can be prepared in a manner known per se, for example either by reacting 3,5-dinitrophthalic anhydride with a compound of the formula IIIa

  (IIIa)

or by reacting 3,5-dinitrophthalic acid with a compound of the formula IIIb

  (IIIb)

in which formulae Y is hydrogen, $-COH$ or $-CO-NH-R$, Y' is $-COH$ or $-CO-NH-R$ and R is as defined under formula I, to give a compound of the formula IV

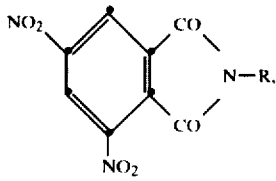  (IV)

reacting the compound of the formula IV with a compound of the formula Va

  (Va), a salt of a compound of the formula Va or mixtures thereof, to give a compound of the formula Ia

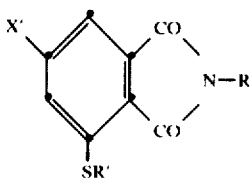  (Ia)

in which X' is $-NO_2$ or $-SR'$ and R and R' are as defined under formula I or II, then, if appropriate, reacting compounds of the formula Ia in which X' is $-NO_2$ with a salt of a compound of the formula Vb or Vc

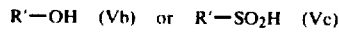

to give a compound of the formula Ib

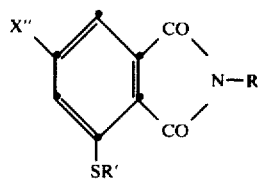  (Ib)

in which R and R' are as defined above and X" is $-OR'$ or $-SO_2R'$, and then, if appropriate, converting the compounds of the formula Ia or Ib to a compound of the formula II.

The compounds of the formula IV are novel and are likewise a subject of the present invention. In this formula, R advantageously has the preferred definitions given above.

The starting compounds (3,5-dinitrophthalic acid, 3,5-dinitrophtalimide, 3,5-dinitrophthalic anhydride, compounds of the formulae IIIa, IIIb and Va and salts of compounds of the formulae Va, Vb and Vc) are known or can be prepared by methods known per se.

The above reactions can be carried out in a manner known per se. The reaction of 3,5-dinitrophthalic anhydride or 3,5-dinitrophthalic acid with the compounds of the formula IIIa or IIIb can be carried out with or without the addition of a suitable inert organic solvent, such as N,N-dimethylformamide or aromatic hydrocarbons, for example toluene or xylenes. If the reaction is carried out in the presence of an inert organic solvent, it is generally performed at the reflux temperature. For carrying out the reaction in the melt (without the addition of solvent), the reaction temperatures are preferably between about 160° and 220° C. In the said reaction, the corresponding amic acids can be formed as intermediates, and these are generally converted to the imides merely by heating. N,N-Dimethylurea is the preferred compound of the formula IIIa or IIIb in which Y or Y' is $-CO-NH-R$. The reaction of 3,5-dinitrophthalic anhydride with a compound of the formula IIIa in which Y is $-COH$ and especially hydrogen is particularly preferred.

The reaction of the 3,5-dinitrophthalimides of the formula IV with the mercaptans of the formula Va or their salts, and also the possible further reaction of compounds of the formula Ia in which $X' = -NO_2$ with salts of compounds of the formula Vb or Vc, are advantageously carried out in the presence of an inert organic solvent, at temperatures between about 0 and the reflux temperature, preferably between about 20° and 50° C. for mercaptans of the formula Va, or their salts, and salts of compounds of the formula Vb, and about 50°-150° C. for the reaction with salts of the formula Vc. Examples of suitable inert organic solvents are aliphatic hydrocarbons which are unsubstituted or substituted by chlorine, such as methylene chloride or chloroform; aliphatic or cyclic ethers, such as diethyl ether, diisopropyl ether, dimethoxyethane, tetrahydrofuran and dioxan; alkyl esters of aliphatic monocarboxylic acids having a total of 2-8 C atoms, such as methyl, ethyl and n-butyl acetates and ethyl and n-butyl butyrates; N,N-dialkylamides of aliphatic monocarboxylic acids having 1-3 C atoms in the acid moiety, such as N,N-dimethylformamide and N,N-dimethylacetamide; dialkyl sulfoxides, such as dimethyl sulfoxide and diethyl sulfoxide; alkylnitriles having 2-5 C atoms, such as acetonitrile and proprionitrile; phosphoric acid amides, such as hexamethylphosphoric acid triamide; and cyclic amides, such as N-methylpyrrolidone.

Suitable salts of compounds of the formulae Va, Vb and Vc are salts wlith either organic or inorganic bases. Alkali metal and quaternary ammonium salts, such as the Na, K, tetramethylammonium, tetraethylammonium, benzyltrimethylammonium and benzyltriethylammonium salts, are preferred. The said salts can be employed as such or formed in situ in a manner known per se. In the latter case, alkali metal acetates or carbonates are advantageously used as bases. The compounds of the formula Va are preferably employed in the form of salts. Sodium phenolates, alcoholates or sulfinates and potassium phenolates, alcoholates or sulfinates are particularly preferred.

The possible hydrolysis of the compounds of the formula Ia or Ib to phthalic acids of the formula II, and their cyclisation to the corresponding anhydrides, can likewise be carried out in a manner known per se. The hydrolysis to the phthalic acids is advantageously carried out in an aqueous medium by the addition of suitable bases, such as NaOH or KOH, at the reflux temperature, the corresponding amic acids being formed initially, and subsequent acidification of the reaction mixture, preferably with a strong acid, such as HCl. The resulting phthalic acids can be cyclised to the anhydrides in a customary manner, namely under the action of heat or with the addition of dehydrating agents. The phthalic acids of the formula II are thus intermediates for the preparation of the corresponding anhydrides. Examples of suitable dehydrating agents are anhydrides of aliphatic $C_{2-5}$-monocarboxylic acids which are unsubstituted or substituted by halogen atoms or $C_1-C_4$-alkyl groups, such as acetic anhydride, propionic anhydride, butyric anhydride, trifluoroacetic and trichloroacetic anhydrides and trimethylacetic and triethylacetic anhydrides; acetyl halides which are unsubstituted or substituted by halogen, such as acetyl chloride, chloroacetyl chloride and dichloroacetyl chloride; and carbodiimides, such as N,N'-diisopropylcarbodiimide and N,N'-dicyclohexylcarbodiimide. Acetic anhydride is the preferred dehydrating agent.

The above reactions can also be carried out without intermediate isolation of the compounds of the formulae IV, Ia or Ib or of the 3,5-dinitrophthalic acids of the formula II. The preparation of compounds of the formula I in which X is —SR' is generally carried out in two stages by initially introducing the —SR' group into the 3-position and subsequently introducing a similar or different group —SR' into the 5-position.

The compounds of the formula I and the phthalic anhydrides of the formula II ($M_1$ and $M_2$ together being —O—) can be employed as sensitisers for photocrosslinkable polymers of the most diverse type.

Polymers of this type are used, for example, for the production of printing plates for the offset printing process, or for the production of photo-offset lacquers for unconventional photography, for example for the production of photographic images by means of photopolymerisation or photocrosslinking. Such polymers are applied especially as so-called photoresists for the production of printed circuits by methods known per se. In this process, that side of the printed circuit board which is provided with the light-sensitive layer is exposed through a negative transparency carrying the printed circuit image and then developed, whereupon the unexposed parts of the layer are removed by means of developing liquid.

The polymers used can be any desired materials of which the photosensitivity (sensitivity towards actinic rays) can be increased by employing the sensitisers according to the invention. The compounds of the formula I and the anhydrides of the formula II are very particularly suitable as sensitisers for polymers of the type described in German Offenlegungsschrift No. 2,626,769, i.e. polymers which have photosensitive groups of the formula VI

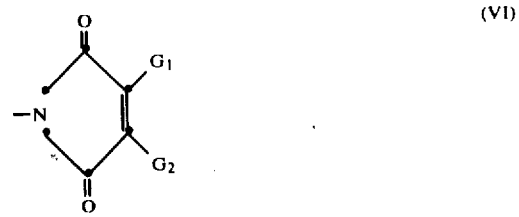

in which $G_1$ and $G_2$ independently of one another are alkyl having 1-4 C atoms, in particular methyl, or $G_1$ and $G_2$ together make up a five- to six-membered carbocyclic ring.

The compounds of the formula I and the phthalic anhydrides of the formula II can be incorporated into the photocrosslinkable polymers in a manner known per se. The content of sensitiser in the polymer can vary widely, depending on the intended application and the number of photocrosslinkable groups present in the polymer, but is generally between 0.1 and 20%, based on the weight of the polymer.

Finally, the compounds of the formula I and the phthalic anhydrides of the formula II are also applied as photoinitiators. The invention therefore also relates to the use of the said compounds, together with amines, as initiators for the photopolymerisation of ethylenically unsaturated compounds or for the photochemical crosslinking of polyolefins.

The organic amines used can be aliphatic, aromatic, araliphatic, cycloaliphatic or heterocyclic amines. They can be primary, secondary or tertiary amines. Examples of these amines are butylamine, dibutylamine, tributylamine, cyclohexylamine, benzyldimethylamine, dicyclohexylamine, triethylamine, phenyl-diethanolamine, piperidine, piperazine, morpholine, pyridine, quinoline, ethyl p-dimethylaminobenzoate or Michler's ketone (4,4'-bis-dimethylamino-benzophenone).

Mixtures of
(A) a compound of the formula I or an anhydride of the formula II, in which formulae R, X and R' have the preferred definitions given above, and
(B) an aliphatic tertiary amine, an alkyl p-dimethylaminobenzoate or Michler's ketone, are preferred.

Examples of aliphatic tertiary amines are trimethylamine, triethylamine, triisopropylamine, tributylamine, dodecyl-dimethylamine, octyl-dimethylamine, triethanolamine, tris-(hydroxypropyl)-amine, N-methyldiethanolamine or N-butyl-diethanolamine. Mixtures of (A) a compound of the formula I or an anhydride of the formula II, in which formulae R, X and R' have the preferred definitions given above, and (B) triethanolamine or a $C_{1-4}$-alkyl-diethanolamine, are particularly preferred.

The said preferred mixtures preferably contain the compounds of the formula I or the anhydrides of the formula II, and the organic amines, in a weight ratio of 4:1 to 1:4.

Examples of photopolymerisable compounds are unsaturated monomers such as acrylic or methacrylic acid esters, for example methyl, ethyl, n- or tert.-butyl, isooctyl or hydroxyethyl acrylate, methyl or ethyl methacrylate, ethylene diacrylate, butanediol diacrylate, hexanediol diacrylate, neopentyl diacrylate, trimethylolpropane triacrylate, pentaerythritol tetraacrylate or pentaerythritol triacrylate; acrylonitrile, methacrylonitrile, acrylamide, methacrylamide or N-substituted (meth)acrylamides; vinyl esters, for example vinyl acetate, propionate, acrylate or succinate; other vinyl compounds, such as vinyl ethers, vinyl ketones, vinyl sulfones, styrene, alkylstyrenes, halogenostyrenes, divinylbenzene, N,N'-divinylurea, vinylnaphthalene, N-vinylpyrrolidone, vinyl chloride or vinylidene chloride, allyl compounds, such as diallyl phthalate, diallyl maleate, triallyl isocyanurate, triallyl phosphate or ethylene glycol diallyl ether, and mixtures of such unsaturated monomers. The mixtures according to the invention are particularly suitable for the photopolymerisation of acrylic acid esters and mixtures thereof.

Further examples are unsaturated acrylic resins. These include, for example, reaction products of polyepoxides (epoxide resins) with acrylic acid or methacrylic acid, or reaction products of polyisocyanates with hydroxyalkyl acrylates, and also the reaction products of polyesters or polyethers containing hydroxyl groups with acrylic or methacrylic acid. These unsaturated acrylic resins are generally used in a mixture with one or more acrylates of a monohydric, dihydric or polyhydric alcohol, for example ethyl, butyl, benzyl, 2-ethylhexyl or 2-hydroxypropyl acrylate, ethylene glycol diacrylate, propylene glycol diacrylate, butanediol diacrylate, hexanediol diacrylate, trimethylolpropane triacrylate or pentaerythritol tetraacrylate.

Photopolymerisable systems consisting of (a) at least one ethylenically unsaturated compound, (b) a mixture, of the type defined, of (A) and (B) and, if appropriate, (c) other additives, such as inhibitors, stabilisers, UV absorbers, fillers, pigments, dyes, thixotropic agents and flow control agents, for example silicone oil, are also a subject of the invention. Hydroquinone, hydroquinone derivatives, p-methoxyphenol or β-naphthols, for example, are used as inhibitors which are intended to protect against premature polymerisation, in particular during the preparation of the systems by mixing of the components. Examples of UV absorbers which can be employed are those of the benztriazole or benzophenone type. Examples of suitable fillers are silicic acid, talc or gypsum.

Preferred photopolymerisable systems are those having the proportions of 99.5–80% by weight of (a) and (c) and 0.5–20% by weight of (b), the compound (A) preferably consisting of a compound of the formula I or an anhydride of the formula II, in which formulae R, X and R' have the preferred definitions given above. An acrylic acid ester or a mixture of several acrylic acid esters is preferably used as the component (a). It is also possible to use combinations with known photoinitiators which form radicals by photofragmentation, for example benzoin ethers, dialkoxyacetophenones or benzil ketals.

The initiator mixtures according to the invention are of great importance for the photocuring of printing inks and white-pigmented layers, because the drying time of the binder is a decisive factor in the production rate of graphic products and should be of the order of magnitude of fractions of a second. The initiators according to the invention are also very suitable for photocurable systems for the production of printing plates. A further field of use is the UV curing of coatings for metal, for example in the lacquering of metal sheets for tubes, cans or bottle caps, and also the UV curing of coatings for plastics, for example of PVC-based floor or wall coverings. An example of the UV curing of coatings for paper is the colourless lacquering of labels, record sleeves or book covers.

The mixture according to the invention can also be used as initiators for the photochemical crosslinking of polyolefins. Examples of polyolefins suitable for this purpose are polypropylene, polybutene, polyisobutylene and also copolymers, for example ethylene/propylene copolymers, but preferably low-, medium- or high-density polyethylene. The addition of the photoinitiators to the photopolymerisable systems is generally carried out by simply stirring them in, because the majority of these systems are liquid or readily soluble. In general, a solution of the initiators is used, thus ensuring the uniform distribution of the initiators and also the transparency of the polymers. The polymerisation is carried out by the known methods of photopolymerisation by irradiation with light which contains a high proportion of radiation of short wavelength. Examples of suitable light sources are medium-pressure, high-pressure and low-pressure mercury-vapour radiators and also superactinic fluorescent tubes, the emission maxima of which are in the range between 250 and 450 nm. In the photochemical crosslinking of polyolefins, the photoinitiator is added to the polyolefin before or during the shaping treatment, for example by mixing in powder form or by mixing with the plasticised polyolefin. The crosslinking is carried out by irradiation of the shaped object in solid form, for example in the form of films of fibres.

Compounds of the formula II in which X is the nitro group and R' is phenyl, carboxyphenyl, halogenophenyl, nitrophenyl, alkyl- or alkoxy-phenyl having in each case 1–4 C atoms in the alkyl or alkoxy moiety, or acetylaminophenyl are also suitable for the preparation of thioxanthones, which in turn are valuable sensitisers for photocrosslinkable polymers. Thioxanthones of this type can be obtained by cyclising the said compounds in a manner known per se, in the presence of a proton acid or a Lewis acid, and, if appropriate, subsequently converting the resulting 3-nitrothioxanthone-1-carboxylic acids to other thioxanthone derivatives, such as esters or amides.

(A) PREPARATION EXAMPLES

Example 1

3,5-Dinitrophthalic acid N-p-toluylimide 2 kg (8.4 mols) of 3,5-dinitrophthalic anhydride and 897 g (8.4 mols) of p-toluidine are kept under reflux in 6.2 liters of glacial acetic acid for 3 hours. After cooling, the mixture is filtered and the residue is washed with 2 liters of water, suspended in 25 liters of water, filtered off and dried at 100° C. in vacuo.

Yield: 2,339 g (85% of theory); melting point: 182°–3° C.

Analysis for $C_{15}H_9N_3O_6$ (molecular weight: 327.25): Calculated: C 55.05%, H 2.77%, N 12.84%. Found: C 55.05%, H 3.02%, N 12.91%.

EXAMPLE 2

3,5-Dinitrophthalic acid N-methylimide (a) 51.22 g (0.2 mole) of 3,5-dinitrophthalic acid and 8.81 g (0.1 mol) of N,N'-dimethylurea are finely ground together and carefully heated to 180° C. in an open flask. The dark, clear melt formed after the foaming has ceased is kept for 6 hours at 180° C. and 1 hour at 200° C.

After cooling, the residue is dissolved in tetrahydrofuran/methylene chloride (volume ratio 1:1), the solution is filtered and the filtrate is evaporated. After recrystallisation from tetrahydrofuran/cyclohexane, 42.37 g (84% of theory) of 3,5-dinitrophthalic acid N-methylimide, with a melting point of 174°–6° C., are obtained. After a further recrystallisation, the product has a melting point of 178°–180° C.

(b) 238.11 g (1 mol) of 3,5-dinitrophthalic anhydride are dissolved under reflux in 1 liter of xylene. 62.02 g (1.05 mols) of N-methylformamide are added dropwise under reflux in the course of 30 minutes. After 18 hours under reflux, the water formed and the formic acid, together with some xylene (total 140 ml), are distilled off, the boiling point rising to 137° C. The solution is filtered hot. After slow cooling and concentration of the mother liquor, 209.42 g (83% of theory) of 3,5-dinitrophthalic acid N-methylimide are obtained; melting point: 174°–6° C.

Analysis for $C_9H_5N_3O_6$ (molecular weight: 251.15): Calculated: C 43.04%, H 2.01%, N 16.73%. Found: C 43.40%, H 2.00%, N 16.5%.

EXAMPLE 3

3,5-Dinitrophthalic acid N-n-butylimide 23.81 g (0.1 mole) of 3,5-dinitrophthalic anhydride are dissolved under reflux in 150 ml of xylene. The mixture is cooled to 105° C. and 7.31 g (0.1 mol) of n-butylamine in 10 ml of xylene are added dropwise, with vigorous stirring. On warming slowly to the reflux temperature, the amic acid which has precipitated out is converted to the soluble product, partly with vigorous foaming. After refluxing for 30 minutes under a water separator, the mixture is cooled and filtered and the mother liquor is evaporated. After recrystallisation from methylene chloride/diethyl ether/n-pentane, 27.53 g (94% of theory) of 3,5-dinitrophthalic acid N-n-butylimide, with a melting point of 40°–42° C., are obtained.

Analysis for $C_{12}H_{11}N_3O_6$ (molecular weight: 293.24): Calculated: C 49.15%, H 3.78%, N 14.33%. Found: C 49.46%, H 3.89%, N 14.35%.

EXAMPLE 4

5-Nitro-3-phenylthiophthalimide 9.48 g (40 mmols) of 3,5-dinitrophthalimide are suspended in 150 ml of ethyl acetate, and 5.55 g (42 mmols) of sodium thiophenolate are then added. After stirring for 18 hours at 25° C., the reaction mixture is evaporated, the residue is taken up in a mixture of methylene chloride and ethyl acetate, and the organic phase is washed with saturated $NaHCO_3$ solution and saturated NaCl solution, dried over sodium sulfate and evaporated. After recrystallisation from methylene chloride/n-hexane, 10.54 g (88% of theory) of 5-nitro-3-phenylthiophthalimide, with a melting point of 207°–209° C., are obtained.

Analysis for $C_{14}H_8N_2O_4S$ (molecular weight: 300.29): Calculated: C 56.00% H 2.69%, N 9.33%, S 10.68%, O 21.31%. Found: C 55.49%, H 2.88%, N 9.56%, S 10.45, O 21.42%.

EXAMPLE 5

5-Nitro-3-phenylthiophthalic acid N-p-toluylimide (a) 820 mg (2.5 mmols) of 3,5-dinitrophthalic acid N-p-toluylimide [prepared according to Example 1], 0.33 g (3 mmols) of thiophenol and 29 mg (0.125 mmols; 5% by weight) of benzyltriethylammonium chloride are dissolved in 15 ml of $CH_2Cl_2$, and a solution of 0.492 g (6 mmols) of anhydrous sodium acetate in 4 ml of water is then added. After stirring vigorously for 20 minutes at 25° C., the mixture is diluted with water and adjusted to pH 9–10 and the organic phase is separated off, washed with 2N NaOH, dried over sodium sulfate and evaporated. After recrystallisation from toluene, 930 mg (95% of theory) of 5-nitro-3-phenylthiophthalic acid N-p-toluylimide, with a melting point of 207°–209° C., are obtained.

(b) 49 g (0.15 mol) of 3,5-dinitrophthalic acid N-p-toluylimide are initially introduced into 500 ml of dimethyl sulfoxide. 22.5 g (0.204 mol) of thiophenol are added dropwise in the course of 10 minutes, at 22°–23° C., with gentle cooling, nitrous gases being formed. After 30 minutes at 25° C., the mixture is kept for 4 hours at 45° C. and discharged into one liter of ice-water, and the precipitate is filtered off, washed with water and dried. After recrystallisation from toluene, 52.5 g (90% of theory) of 5-nitro-3-phenylthiophthalic acid N-p-toluylimide, with a melting point of 208°–9° C., are obtained.

Analysis for $C_{21}H_{14}N_2O_4S$ (molecular weight: 390.40): Calculated: C 64.61%, H 3.62%, N 7.18%, S 8.21%. Found: C 64.30%, H 3.81%, N 7.32%, S 8.45%.

EXAMPLE 6

3-(3,4-Dichlorophenylthio)-5-nitrophthalic acid N-methylimide 20.09 g (80 mmols) of 3,5-dinitrophthalic acid N-methylimide [prepared according to Example 2] are initially introduced into 300 ml of ethyl acetate and treated with 33.6 g (243 mmols) of ground, anhydrous potassium carbonate, and 15.04 g (84 mmols) of 3,4-dichlorothiophenol are then added dropwise at 25° C. After the addition of 100 ml of tetrahydrofuran, the mixture is stirred overnight and evaporated to dryness and the residue is taken up in a mixture of methylene chloride and dilute hydrochloric acid. The organic phase is washed with saturated NaCl solution, dried over sodium sulfate and evaporated. After recrystallisation from methylene chloride/n-pentane, 25.74 g (84% of theory) of the title imide, with a melting point of 167°–8° C., are obtained.

Analysis for $C_{15}H_8Cl_2N_2O_4S$ (molecular weight: 383.21): Calculated: C 47.02%, H 2.11%, N 7.31%. Found: C 46.87%, H 2.15%, N 7.43%.

EXAMPLE 7

3-Ethylthio-5-nitrophthalic acid N-methylimide 5.02 g (20 mmols) of 3,5-dinitrophthalic acid N-methylimide, 2.73 g (44 mmols) of ethylmercaptan, 8.2 g (1 0 mmols) of anhydrous sodium acetate and 50 ml of ethyl acetate are kept at 25° C. overnight and then kept under reflux, again overnight. The reaction mixture is evaporated, the residue is taken up in methylene chloride/water, the extracts are washed with saturated $NaHCO_3$ solution, dried over sodium sulfate and evaporated and the residue is chromatographed with methylene chloride over 20 g of silica gel. After recrystallisation from methylene chloride/n-pentane, 2.40 g (45% of theory) of 3-ethylthio-5-nitrophthalic acid N-methylimide, with a melting point of 193°–4° C., are obtained.

Analysis for $C_{11}H_{10}N_2O_4S$ (molecular weight: 266.27): Calculated: C 49.62%, H 3.79%, N 10.52%, S 12.04%. Found: C 49.78%, H 3.83%, N 10.71%, S 11.97%.

EXAMPLE 8

3-n-Butylthio-5-nitrophthalic acid N-methylimide 25.1 g (100 mmols) of 3,5-dinitrophthalic acid N-methylimide, 19.8 g (220 mmols) of n-butylmercaptan, 41.5 g (300 mmols) of anhydrous potassium carbonate and 250 ml of absolute tetrahydrofuran are kept under reflux overnight. The reaction mixture is filtered, the filtrate is evaporated and the residue is taken up in methylene chloride/2N HCl. The extracts are washed with saturated NaCl solution, dried over sodium sulfate and evaporated. After recrystallisation from cyclohexane, 11.96 g (41% of theory) of the title imide are obtained; melting point: 106°–108° C.

Analysis for $C_{13}H_{14}N_2O_4S$ (molecular weight: 294.33): Calculated: C 53.05% H 4.80%, N 9.52%, S 10.90%. Found: C 53.30%, H 4.90%, N 9.01%, S 11.29%.

EXAMPLE 9

3-n-Decylthio-5-nitrophthalic acid N-methylimide 20 g (79.6 mmols) of 3,5-dinitrophthalic acid N-methylimide and 21 g (107 mmols) of sodium n-dodecylmercaptide are stirred for 2 hours at 40° C. in 100 ml of ethyl acetate. After evaporation, the residue is extracted with methylene chloride/dilute hydrochloric acid and the organic phase is washed with saturated NaCl solution, dried over sodium sulfate and evaporated. After recrystallisation from methanol/diethyl ether, 23.24 g (77% of theory) of the title imide (yellow product), with a melting point of 85°–86° C., are obtained.

Analysis for $C_{19}H_{26}N_2O_4S$ (molecular weight: 378.49): Calculated: C 60.29%, H 6.92%, N 7.40%, S 8.47%. Found: C 60.28%, H 6.71%, N 7.39%, S 8.19%.

EXAMPLE 10

3-n-$C_8F_{17}$—$CH_2CH_2$-thio-5-nitrophthalic acid N-p-toluylimide 20 g (0.06 mol) of 3,5-dinitrophthalic acid N-p-toluylimide, 32.3 g (0.0673 mol) of n-$C_8F_{17}(CH_2)_2$—SH, 12.7 g (0.092 mol) of potassium carbonate and 250 ml of absolute dioxan are stirred for 42 hours at 25° C. The reaction mixture is concentrated, the residue is taken up in water and the mixture is extracted three times with $CH_2Cl_2$. The extracts are washed with water, dried over sodium sulfate and concentrated. After recrystallisation from toluene, 44.7 g (98% of theory, of the title imide are obtained in the form of yellowish flakes; melting point 169°–171° C.

Analysis for $C_{25}H_{13}F_{17}N_2O_4S$ (molecular weight: 760.42): Calculated: C 39.49%, H 1.72%, F 42.47%. N 3.68%, S 4.22%. Found: C 39.55%, H 1.65%, F 42.50%, N 3.80%, S 4.40%.

EXAMPLE 11

3-n-Decylthio-5-n-$C_8F_{17}(CH_2)_2$-thiophthalic acid N-methylimide 13.07 g (34.6 mmols) of 3-n-decylthio-5-nitrophthalic acid N-methylimide [prepared according to Example 9], 18.35 g (38.2 mmols) of n-$C_8F_{17}(CH_2)_2$—SH, 14.3 g of ground, anhydrous potassium carbonate and 450 ml of N,N-dimethylformamide are stirred for 18 hours at 25° C. and the reaction mixture is evaporated. The residue is taken up in methylene chloride/dilute hydrochloric acid. The organic phase is washed with saturated NaCl solution, dried over sodium sulfate and evaporated. After recrystallisation from toluene, 25.04 g (89% of theory) of the title imide, with a melting point of 117°–8° C., are obtained.

Analysis for $C_{29}H_{30}F_{17}NO_2S_2$ (molecular weight: 811.65): Calculated: C 42.91%, H 3.73%, N 1.73%, S 7.90%, F 39.79%. Found: C 42.44%, H 3.53%, N 1.73%, S 8.08%, F 40.52%.

EXAMPLE 12

3,5-Bis-(n-$C_8F_{17}(CH_2)_2$)-thiophthalic acid N-p-toluylimide 184.6 g (0.243 mol) of 5-nitro-3-n-$C_8F_{17}(CH_2)_2$-thiophthalic acid N-p-toluylimide, 116.6 g (0.243 mol) of n-$C_8F_{17}(CH_2)_2$—SH, 100.75 g (0.729 mol) of potassium carbonate and 1.8 liters of N,N-dimethylformamide (DMF) are stirred for 30 minutes at 25° C. The reaction mixture is evaporated in portions (vigorous foaming), the residue is extracted with $CH_2Cl_2$/acetone/water and the organic phase is washed with water, dried over sodium sulfate and evaporated. After recrystallisation from ethyl acetate, 266 g (91% of theory) of the title imide are obtained; melting point 144°–6° C.

Analysis for $C_{35}H_{17}F_{34}NO_2S_2$ (molecular weight: 1,193.58): Calculated: C 35.22%, H 1.44%, F 54.12%, N 1.17%, S 5.37%. Found: C 35.0%, H 1.5%, F 54.2%, N 1.2%, S 5.5%.

EXAMPLE 13

5-n-Decylthio-3-n-$C_8F_{17}(CH_2)_2$-thiophthalic acid N-p-toluylimide 3 g (3.95 mmols) of 5-nitro-3-n-$C_8F_{17}(CH_2)_2$-thiophthalic acid N-p-toluylimide, 0.70 g (4.34 mmols) of n-decanethiol, 1.60 g (11.85 mmols) of potassium carbonate and 35 ml of DMF are stirred for 17 hours at 25° C. The mixture is evaporated, the residue is taken up in water/$CH_2Cl_2$ and the organic phase is washed with water, dried over $Na_2SO_4$ and evaporated. After recyrstallisation from ethyl acetate, 3.0 g (86% of theory of the title imide, with a melting point of 117°–9° C., are obtained.

Analysis for $C_{35}H_{34}F_{17}NO_2S_2$ (molecular weight: 887.75) Calculated: C 47.35%, H 3.86%, F 36.38%, N 1.58%, S 7.22%. Found: C 47.4%, H 3.7%, F 36.6%, N 1.6%, S 7.1%.

EXAMPLE 14

3,5-Bis-(phenylthio)-phthalic acid N-p-toluylimide 3.9 g (10 mmols) of 5-nitro-3-phenylthiophthalic acid N-p-toluylimide, 1.4 g (10 mmols) of sodium thiophenolate and 80 ml of dimethyl sulfoxide are stirred for one hour at 25° C. The reaction mixture is taken up in water and chloroform and the organic phase is washed with water, dried over magnesium sulfate and evaporated. After recrystallisation from toluene, 4.1 g (91% of theory) of the title imide, with a melting point of 179°–180° C., are obtained.

Analysis for $C_{27}H_{19}NO_2S_2$ (molecular weight: 453.57): Calculated: C 71.50%, H 4.22%, N 3.09%, S 14.14%.
Found: C 71.30%, H 4.40%, N 3.20%, S 14.00%.

EXAMPLE 15

5-Methoxy-3phenylthiophthalic acid N-p-toluylimide 110 ml of 1.0 M sodium methylate solution in 110 mmols of absolute methanol are evaporated to dryness and the residue is suspended in 200 ml of dimethyl sulfoxide. 39.04 g (100 mmols) of 5-nitro-3-phenylthiophthalic acid N-p-toluylimide in 200 ml of dimethyl sulfoxide are added, the mixture is stirred for one day at 25° C. and then discharged into 1.5 liters of dilute hydrochloric acid and the resulting mixture is extracted with chloroform. The organic phase is washed three times with water, dried over sodium sulfate and evaporated. After recrystallisation from toluene/cyclohexane, 31.68 g (84% of theory) of the title imide, with a melting point of 166°–168° C., are obtained.

Analysis for $C_{22}H_{17}NO_2S$ (molecular weight: 375.44) Calculated: C 70.38%, H 4.57%, N 3.73%, S 8.54%. Found: C 70.31%, H 4.58%, N 3.79%, S 8.33%.

EXAMPLE 16

3-n-Decylthio-5-phenylsulfonylphthalic acid N-methylimide 2.0 g (5.28 mmols) of 3-n-decylthio-5-nitrophthalic acid N-methylimide, 1.73 g (10.57 mmols) of sodium phenylsulfinate and 20 ml of DMF are stirred for 17 hours at 120° C. The mixture is concentrated and the residue is taken up in methylene chloride/dilute hydrochloric acid. The organic phases are washed with saturated NaCl solution, dried over sodium sulfate and evaporated. After recrystallisation from cyclohexane, 1.83 g (73% of theory) of the title imide, with a melting point of 86°–88° C., are obtained.

Analysis for $C_{25}H_{31}NO_4S_2$ (molecular weight: 473.65): Calculated: C 63.40%, H 6.60%. Found: C 63.17%, H 6.39%.

EXAMPLE 17

3-n-Butylthio-5-nitrophthalic anhydride 883 mg (3 mmols) of 3-n-butylthio-5-nitrophthalic acid N-methylimide are kept under reflux overnight in 9 ml of 1N sodium hydroxide solution and the mixture is acidified with 10 ml of 2N hydrochloric acid and, after 5 minutes under reflux, cooled. The mixture is extracted with tetrahydrofuran/toluene and the extracts are washed with saturated NaCl solution, dried over sodium sulfate and evaporated. The resulting acid is converted to the anhydride with 1 ml of acetic anhydride and 10 ml of toluene, by heating and evaporation. After recrystallisation from cyclohexane, 790 mg (94% of theory) of the title anhydride are obtained as a yellow product; melting point: 95°–97° C.

Analysis for $C_{12}H_{11}NO_5S$ (molecular weight: 281.28): Calculated: C 51.24%, H 3.94%, N 4.98%, S 11.40%. Found: C 51.55%, H 3.91%, N 5.14%, S 11.12%.

EXAMPLE 18

3,5-Bis-(n-$C_8F_{17}(CH_2)_2$)-thiophthalic anhydride 266.05 g (0.223 mol) of 3,5-bis-(n-$C_8F_{17}(CH_2)_2$)-thiophthalic acid N-p-toluylimide are kept under reflux for one day in 1.2 liters of 20% NaOH, with stirring, and the reaction mixture is then cooled and filtered. The residue is ground, stirred with 2N HCl solution and filtered off. The amic acid obtained in this way is heated with 1.8 liters of concentrated HCl for 5 hours at 120° C., the mixture is cooled and the precipitate is filtered off, washed with water and dried. The resulting mixture of acid and anhydride is completely converted to the anhydride by warming with acetic anhydride and evaporation. After recrystallisation from ethyl acetate, 201 g (81% of theory) of the title anhydride, with a melting point of 151°–154° C., are obtained.

Analysis for $C_{28}H_{10}F_{34}O_3S_2$ (molecular weight: 1,104.44): Calculated: C 30.45%, H 0.91%, F 58.49%, S 5.81%. Found: C 30.1%, H 0.7%, F 58.1%, S 6.2%.

EXAMPLE 19

5-n-Decylthio-3-n-$C_8F_{17}(CH_2)_2$-thiophthalic anhydride 0.50 g (0.564 mmols) of 5-n-decylthio-3-n-$C_8F_{17}$—$(CH_2)_2$-thiophthalic acid N-p-toluylimide and 6 ml of 20% NaOH are stirred overnight at 120° C. After cooling, the mixture is filtered and the precipitate is heated under reflux in 5 ml of concentrated HCl for 3.5 hours. After cooling, the mixture is filtered and the precipitate is washed with water and recrystallised from isopropanol and n-hexane. Yield of (directly formed) anhydride=260 mg (60% of theory); melting point: 110°–111° C.

Analysis for $C_{28}H_{27}F_{17}O_3S_2$ (molecular weight: 798.61): Calculated: C 42.11%, H 3.40%, F 40.44%, S 8.03%. Found: C 42.45%, H 3.45%, F 40.75%, S 7.75%.

EXAMPLE 20

3-n-Decylthio-5-n-$C_8F_{17}(CH_2)_2$-thiophthalic anhydride 3.0 g (3.3 mmols) of 3-n-decylthio-5-n-$C_8F_{17}(CH_2)_2$-thiophthalic acid N-methylimide are stirred vigorously under reflux in 40 ml of 2N NaOH for 18 hours and the mixture is then acidified at 0° C. with 50 ml of concentrated hydrochloric acid. After stirring for 5 hours under reflux, the mixture is cooled and extracted with tetrahydrofuran/toluene (volume ratio 1:3). The extracts are dried over sodium sulfate and evaporated. The residue is converted to the anhydride under reflux with 10 mmols of acetic anhydride in toluene, the solution is filtered and the filtrate is concentrated. After recrystallisation from hot n-hexane, 1.68 g (64% of theory) of the title anhydride are obtained; melting point 116°–7° C.

Analysis for $C_{28}H_{27}F_{17}O_3S_2$ (molecular weight: 798.608): Calculated: C 42.11%, H 3.40%, F 40.44%, S 8.03%. Found: C 42.36%, H 3.36%, F 40.91%, S 8.12%.

EXAMPLE 21

5-Nitro-3-phenylthiophthalic acid (a) 160 g (0.41 mol) of 5-nitro-3-phenylthiophthalic acid N-p-toluylimide are kept under reflux overnight in 1,590 ml of 20% sodium hydroxide solution, with stirring. The mixture is acidified with concentrated hydrochloric acid, with good cooling (10°–15° C.), and the amic acid is filtered off and stirred under heavy reflux with 1,070 ml of concentrated hydrochloric acid for 3 hours. After cooling, the mixture is filtered, the residue is stirred in 650 ml of 5% $Na_2CO_3$ solution, the resulting mixture is filtered and the filtrate is acidified. After cooling, filtration and drying in vacuo over phosphorus pentoxide, 116.2 g (89% of theory) of 5-nitro-3-phenylthiophthalic acid are obtained; melting point: 183°–5° C.

(b) 3.0 g (10 mmols) of 5-nitro-3-phenylthiophthalimide are kept under reflux in 30 ml of 1N sodium hydroxide solution for 8 hours, the mixture is cooled, acidified with 3 ml of concentrated hydrochloric acid and extracted with tetrahydrofuran/toluene and the extracts are washed with saturated NaCl solution, dried over sodium sulfate and evaporated. After drying, 3.13 g (98% of theory) of 5-nitro-3-phenylthiophthalic acid are obtained; melting point: 182°–4° C.

Analysis for $C_{14}H_9NO_6S$ (molecular weight: 319.29): Calculated: C 52.67%, H 2.84%, N 4.39%, S 10.04%. Found: C 52.90%, H 3.20%, N 4.30%, S 9.80%.

EXAMPLE 22

5-Nitro-3-phenylthiophthalic anhydride (a) 4.3 g (13.5 mmols) of 5-nitro-3-phenylthiophthalic acid [prepared according to Example 21] are kept under reflux with 4.1 g (40.2 mmols) of acetic anhydride in 100 ml of toluene for 1 hour. After evaporation, and recrystallisation from methylene chloride/n-pentane, 3.97 g (98% of theory) of 5-nitro-3-phenylthiophthalic anhydride are obtained; melting point: 167°–9° C.

(b) 5 g (21 mmols) of 3,5-dinitrophthalic anhydride are dissolved in 17 ml of tetrahydrofuran; 2.78 g (25.2 mmols) of thiophenol and 4.3 g (42 mmols) of acetic anhydride are then added. This solution is added dropwise, with vigorous stirring, to a mixture of 22.4 g of 30% sodium hydroxide solution, 47.8 mg (0.21 mmol) of benzyltriethylammonium chloride and 100 ml of methylene chloride.

After stirring for 2 hours, the mixture is diluted with water. Neutral impurities are extracted with methylene chloride, the aqueous phase is then acidified and extracted with methylene chloride and the extracts are dried over sodium sulfate and evaporated. The residue is heated with acetic anhydride and toluene and, after evaporation, and recrystallisation from methylene chloride/n-pentane, 2.57 g (41% of theory) of 5-nitro-3-phenylthiophthalic anhydride are obtained; melting point: 167°–9° C.

Analysis for $C_{14}H_7NO_5S$ (molecular weight: 301.27): Calculated: C 55.82%, H 2.34%, N 4.65%, S 10.64%. Found: C 55.8%, H 2.4%, N 4.7%, S 10.5%.

EXAMPLE 23

3-(3,4-Dichlorophenylthio)-5-nitrophthalic anhydride 18.84 g (75 mmols) of 3,5-dinitrophthalic acid N-methylimide [prepared according to Example 2] are initially introduced into 250 ml of ethyl acetate and treated with 30.4 g (220 mmols) of ground, anhydrous potassium carbonate, and 14 g (78 mmols) of 3,4-dichlorothiophenol are then added dropwise. After the addition of 95 ml of tetrahydrofuran, the mixture is stirred overnight and then evaporated to dryness. The residue is kept under reflux overnight in 100 ml of water, the mixture is extracted at 25° C. with petroleum ether and filtered and the aqueous filtrate is acidified with 300 ml of 2N HCl and heated under reflux. After 2.5 hours, the mixture is cooled and extracted with tetrahydrofuran/toluene and the extract is washed with saturated NaCl solution, dried over sodium sulfate and evaporated. The residue is warmed to the reflux temperature with 100 ml of toluene and 7.66 g (75 mmols) of acetic anhydride and, after cooling, the mixture is evaporated. After recrystallisation from methylene chloride/n-pentane, 22.2 g (80% of theory) of 3-(3,4-dichlorophenylthio)-5-nitrophthalic anhydride are obtained; melting point: 154°–7° C.

Analysis for $C_{14}H_5Cl_2NO_5S$ (molecular weight: 370.16): Calculated: C 45.43%, H 1.36%, N 3.78%. Found: C 45.39%, H 1.28%, N 3.93%.

EXAMPLE 24

3-(p-Methylphenylthio)-5-nitrophthalic anhydride 46.05 g (0.180 mol) of 3,5-dinitrophthalic acid are kept under reflux with 26 g (0.25 mol) of acetic anhydride in 210 ml of toluene for one hour. The mixture is filtered hot and the filtrate is evaporated. The residue is dissolved under reflux together with 27.4 g (0.221 mol) of p-thiocresol and 34.7 g (0.34 mol) of acetic anhydride in 4.6 liters of methylene chloride. This solution is added dropwise, at 20°–27° C., with vigorous stirring, to a solution of 1.9 g (8.5 mmols) of benzyltriethylammonium chloride in 190.4 g of 50% potassium hydroxide solution (1.7 mols). After the dropwise addition (135 minutes), the mixture is stirred thoroughly for 90 minutes and acidified with concentrated hydrochloric acid, with cooling. The mixture is converted to two clear phases with the addition of water and acetone; the organic phase is separated off, dried over sodium sulfate and evaporated. The residue is heated under reflux with 36.7 g of acetic anhydride in 200 ml of toluene, the mixture is filtered hot and the filtrate is evaporated. The above reaction is repeated with the residue, using 21.8 g (0.214 mol) of acetic anhydride, 19.9 g (0.161 mol) of p-thiocresol, 2.4 g of benzyltriethylammonium chloride and 285 g of 30% NaOH solution. After thorough stirring, off, dried over sodium sulfate and evaporated. The residue is converted to the anhydride with 52.1 g of acetic anhydride and 250 ml of toluene. After recrystallisation from methylene chloride/n-pentane, 20.83 g (39% of theory) of 3-(p-methylphenylthio)-5-nitrophthalic anhydride are obtained; melting point: 180°–2° C.

Analysis for $C_{15}H_9NO_5S$ (molecular weight: 315.30): Calculated: C 57.14%, H 2.88%, N 4.44%, S 10.17%. Found: C 57.3%, H 3.0%, N 4.5%, S 10.1%.

EXAMPLE 25

3-(p-Methoxyphenylthio)-5-nitrophthalic anhydride 12.17 g (51.1 mmols) of 3,5-dinitrophthalic anhydride are dissolved in 1,350 ml of methylene chloride, and 10.7 g (76.6 mmols) of 4-methoxythiophenol and 10.2 g (100 mmols) of acetic anhydride are then added. This solution is added dropwise, at 20°–24° C., with vigorous stirring, to a mixture of 1.2 g of benzyltriethylammonium chloride, 68.6 g of 33% KOH solution (408 mmols) and 50 ml of methylene chloride.

After 2 hours, the mixture is acidified with hydrochloric acid and extracted with methylene chloride and the extract is dried over sodium sulfate and evaporated. The residue is converted to the anhydride under reflux with 5.3 g of acetic anhydride in 100 ml of toluene. The solution is filtered hot and the mother liquor is evaporated. The dark residue is extracted several times by boiling with cyclohexane. After evaporation, 5.15 g (31% of theory) of 3-(p-methoxyphenylthio)-5-nitrophthalic anhydride are obtained; melting point: 143–48° C.

Analysis for $C_{15}H_9NO_6S$ (molecular weight: 331.30):Calculated: C 54.38%, H 2.74%, N 4.23%, S 9.68%. Found: C 54.40%, H 2.90%, N 4.30%, S 9.50%.

EXAMPLE 26

5-Nitro-3phenylthiophthalic acid N-n-butylimide 7.05 g (24.04 mmols) of 3,5-dinitrophthalic acid N-n-butylimide, 2.73 g (25.24 mmols) of thiophenol, 6.64 g (48.08 mmols) of potassium carbonate and 40 ml of tetrahydrofuran are stirred for 2 hours at 25° C. The mixture is concentrated, the residue is taken up in 2N HCl solution and the resulting mixture is extracted with methylene chloride. After washing with saturated sodium chloride solution, the extract is dried over sodium sulfate and evaporated. By recrystallisation from toluene/cyclohexane, 8.36 g (97% of theory) of 5-nitro-3-phenylthiophthalic acid N-n-butylimide are obtained; melting point: 148°–9° C.

Analysis for $C_{18}H_{16}O_4N_2O$ (molecular weight: 356.40): Calculated: C 60.66%, H 4.53%, N 7.86%, S 9.00%. Found: C 60.49%, H 4.46%, N 7.81%, S 8.90%.

EXAMPLE 27

3-(2-Carboxyphenylthio)-5-nitrophthalic acid N-n-butylimide 1.47 g (5 mmols) of 3,5-dinitrophthalic acid N-n-butylimide, 1.24 g (6 mmols) of disodium thiosalicylate and 15 ml of tetrahydrofuran are stirred under reflux for 5 hours. The mixture is cooled and taken up in 2N HCl solution/tetrahydrofuran/toluene. The organic phase is dried over sodium sulfate and evaporated. Recrystallisation from toluene gives 1.80 g (90% of theory) of 3-(2-carboxyphenylthio)-5-nitrophthalic acid N-n-butylimide; melting point: 192°–6° C.

Analysis for $C_{19}H_{16}N_2O_6S$ (molecular weight: 400.41): Calculated: C 57.00% H 4.03% N 7.00% S 8.01% Found: C 56.82% H 4.10% N 6.95% S 7.72%.

EXAMPLE 28

3-(2-Carboxyphenylthio)-5-n-decylthiophthalic acid N-n-butylimide 20 g (49.9 mmols) of 3-(2-carboxyphenylthio)-5-nitrophthalic acid N-n-butylimide, 9.07 g (54.89 mmols) of n-decanethiol, 27.58 g (199.6 mmols) of potassium carbonate and 500 ml of N,N-dimethylformamide are stirred at 25° C. for 2 hours. The mixture is concentrated and the residue is taken up in methylene chloride/2N HCl solution. The organic phase is washed with saturated NaCl solution, dried over sodium sulfate and concentrated. By recrystallisation from cyclohexane, 23.56 g (93% of theory) of 3-(2-carboxyphenylthio)-5-n-decylthiophthalic acid N-n-butylimide are obtained; melting point: 113°–5° C.

Analysis for $C_{29}H_{35}NO_4S_2$ (molecular weight: 525.72): Calculated: C 66.26%, H 6.71%, N 2.66%. Found: C 65.64%, H 7.17%, N 2.64%.

EXAMPLE 29

3-(2-Carboxyphenylthio)-5-phenylthiophthalic acid N-n-butylimide 12.81 g (32 mmols) of 3-(2-carboxyphenylthio)-5-nitrophthalic acid N-n-butylimide are dissolved in 120 ml of N,N-dimethylformamide. 3.88 g (35.2 mmols) of thiophenol and 13.27 g (96 mmols) of potassium carbonate are then added. After stirring for 30 minutes at 25° C., the mixture is evaporated, the residue is taken up in methylene chloride and the organic phase is washed with 2N HCl solution and with saturated NaCl solution, dried over sodium sulfate and evaporated. After recrystallisation from toluene/cyclohexane, 13.52 g (91% of theory) of the title imide are obtained; melting point: 156°–7° C.

Analysis for $C_{25}H_{21}NO_4S_2$ (molecular weight 463.57): Calculated: C 64.77%, H 4.57%, N 3.02%, S 13.83%. Found: C 64.96%, H 4.73%, N 3.20%, S 13.62%.

(B) APPLICATION EXAMPLES

EXAMPLE I

Preparation of thioxanthones (A) Preparation of thioxanthones (a) 12.7 g (40.3 mmols) of 3-(p-methylphenylthio)-5-nitrophthalic anhydride and 16.1 g (121 mmols) of aluminium trichloride are heated slowly to 120° C. in 120 ml of 1,1,2,2-tetrachloroethane. After cooling, the mixture is evaporated, the residue is stirred in dilute hydrochloric acid and the product is filtered off and dried. After recrystallisation from isopropanol, 7.37 g (58% of theory) of 7-methyl-3-nitrothioxanthone-1-carboxylic acid are obtained; melting point > 250° C.

(b) 3.2 g (10.15 mmols) of 7-methyl-3-nitrothioxanthone-1-carboxylic acid are kept under reflux with 20 ml of oxalyl chloride for 5 hours. After evaporation, 20 ml of n-butanol are added dropwise, with ice-cooling, and the mixture is warmed under reflux for 30 minutes. After concentration from toluene/cyclohexane, 2.7 g (72% of theory) of n-butyl 7-methyl-3-nitrothioxanthone-1-carboxylate are obtained; melting point 164°–7° C.

(c) 1 g (3.17 mmols) of 7-methyl-3-nitrothioxanthone-1-carboxylic acid is suspended in 15 ml of methylene chloride. Then 2 drops of pyridine are added and 0.56 g (4.76 mmols) of thionyl chloride is added dropwise. After 2 hours under reflux, the clear solution is concentrated and the residue is treated with 5 ml of benzene. A solution of 0.7 g (951 mmols) of n-butylamine in benzene is then added dropwise. After stirring for 30 minutes at 25° C., the mixture is concentrated, the residue is taken up in methylene chloride/water and the organic phase is dried over sodium sulfate and evaporated. After recrystallisation from methylene chloride/n-pentane, 0.68 g of 7-methyl-3-nitrothioxanthone-1-carboxylic acid N-n-butylamide (58% of theory) are obtained; melting point > 250° C.

EXAMPLE II (a) Preparation of polymers

Polymers having the following structure and composition are prepared:

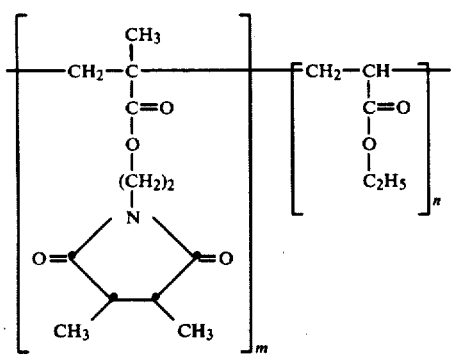

$$\frac{m}{m+n} = 0.8$$

$$\frac{n}{m+n} = 0.2$$

465.5 g (1.963 mols) of dimethylmaleic acid N-β-(methacryloyloxy)-ethylimide [prepared according to German Offenlegungsschrift No. 2,626,769] are dissolved together with 49.15 g (0.49 mol) of ethyl acrylate in 960 ml of 1-acetoxy-2-ethoxyethane, under nitrogen. At 80° C., a solution of 3.86 g of azoisobutyronitrile in 25 ml of 1-acetoxy-2-ethoxyethane is run in under a nitrogen atmosphere and polymerisation is then carried out for 6 hours. Whilst still hot, the solution is stabilised with 2.57 g of 2,6-di-tert.-butyl-p-cresol. The average molecular weight of the polymers obtained in this way (determined by light scattering measurement in CHCl₃) and their limiting viscosity $\eta_{limiting}$ are:

|  | Average molecular weight (light scattering measurement in CHCl₃) | $\eta_{limiting}$ dl/g | (CHCl₃) |
|---|---|---|---|
| Polymer No. 1 | $3 \times 10^6$ | 0.8 | 20° C. |
| Polymer No. 2 | $4.36 \times 10^5$ | 0.29 | 20° C. |

(b) Production of images

The amounts of sensitiser given in the following Tables I and II are added to 10 g of each of the polymer solutions in 1-acetoxy-2-ethoxyethane described above, diluted with N,N-dimethylformamide, the amount (concentration) being based on the solids content. The polymer solutions with the dissolved sensitiser are applied to copper-laminated epoxide plates, by whirler-coating (500 rpm for 1 minute), in such a way that, after drying (15 minutes at 80° C.), a 1-3μ thick polymer layer is formed on the copper. The coated plates are exposed through a negative original (step wedge: Stouffer 21-Step-Sensitivity-Guide) with a 400 watt high-pressure mercury-vapour lamp at a distance of 55 cm from the vacuum table. (Vacuum table with 8 mm thick Pyrex glass filter fitted in front; exposure times, see Tables I and II).

After exposure, the image is developed in a 1,1,1-trichloroethane bath for 2 minutes, the non-crosslinked parts being dissolved away. The resulting relief image of the step wedge reproduced is revealed by etching the bare copper parts with a 50% FeCl₃ solution. In the following Tables I and II, $S_{rel}$ is the relative sensitivity. It is a factor which indicates by how much the exposure time must be longer or shorter than 3 minutes so that step 7 (optical density of the step wedge=1) is still reproduced. The following relationship applies:

$$S_{rel} = \frac{1}{\sqrt{2}^{7-X}},$$

X being the step which is actually reproduced after exposure for 3 minutes. The determination of $S_{rel}$ is based on the method described by W. S. De Forest ("Photoresist", Mc Graw Hill Book Company, New York, 1975, pages 113 et seq.) for determining the photosensitivity.

TABLE I

| Sensitiser | λ max. | ε max. | Concentration % by weight | mol % | Photosensitivity last step reproduced after 10″ | 30″ | 1′ | 3′ | 6′ | 12′ | $S_{rel}$ |
|---|---|---|---|---|---|---|---|---|---|---|---|
| Polymer 1, exposed with 400 watt high-pressure mercury-vapour lamp | | | | | | | | | | | |
| 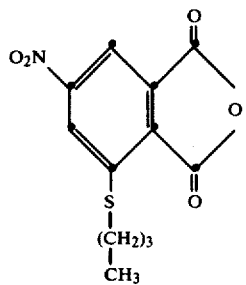 | 410 | 3,000 | 1.41 | 0.005 | 3 | 5 | 7 | 11 | | | 4.0 |

TABLE I-continued
| Sensitiser | λ max. | ε max. | Concentration % by weight | mol % | Photosensitivity last step reproduced after |  |  |  |  |  | $S_{rel}$ |
|---|---|---|---|---|---|---|---|---|---|---|---|
|  |  |  |  |  | 10" | 30" | 1' | 3' | 6' | 12' |  |
| 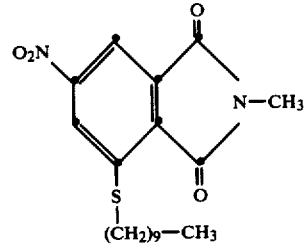 | 410 | 3,000 | 1.89 | 0.005 | 5 | 8 | 10 | 12 |  |  | 5.66 |
| 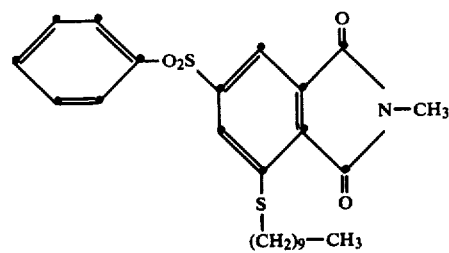 | 388 | 3,300 | 2.37 | 0.005 | 4 | 6 | 9 | 12 |  |  | 5.66 |
| 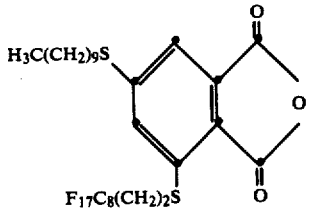 | 335<br>275 | 7,300<br>18,800 | 3.99 | 0.005 |  | 6 | 9 | 11 | 13 |  | 4.0 |
| 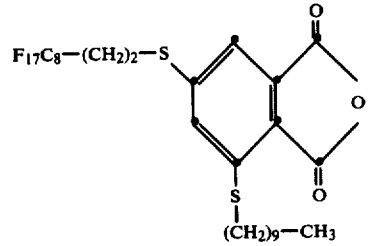 | 3.0 | 4,100 | 3.99 | 0.005 | 4 | 6 | 8 | 12 |  | 5.66 |  |
| 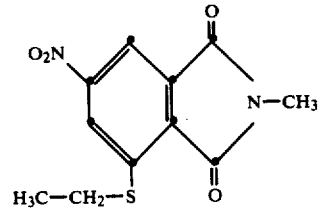 | 406 | 3,200 | 1.33 | 0.005 | 5 | 7 | 9 | 12 |  |  | 5.66 |
| 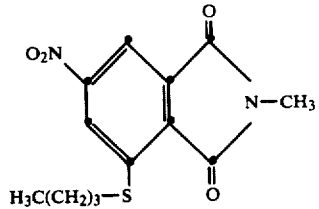 | 404 | 2,840 | 1.42 | 0.005 |  | 4 | 7 | 9 | 12 |  | 5.66 |

TABLE I-continued

Polymer 1, exposed with 400 watt high-pressure mercury-vapour lamp

| Sensitiser | λ max. | ε max. | Concentration % by weight | mol % | Photosensitivity last step reproduced after 10" | 30" | 1' | 3' | 6' | 12' | $S_{rel}$ |
|---|---|---|---|---|---|---|---|---|---|---|---|
|  | 392 | 3,440 | 1.91 | 0.005 |  |  | 3 | 5 | 7 | 11 | 4.0 |

TABLE II

Polymer 2, exposed with 400 watt high-pressure mercury-vapour lamp

| Sensitiser | λ max. | ε max. | Sensitiser Concentration % by weight | mol % | Photosensitivity last step reproduced after 1' | 3' | 6' | 12' | $S_{rel}$ |
|---|---|---|---|---|---|---|---|---|---|
|  | 398 | 3,440 | 1.50 | 0.005 | 1 | 5 | 7 | 9 | 0.5 |
|  | 420 | 4,000 | 1.58 | 0.005 | 3 | 6 | 8 |  | 0.71 |
|  | 420 | 4,150 | 1.86 | 0.005 | 4 | 8 | 10 |  | 1.41 |

Example III

A clear lacquer is prepared according to the following formulation:

30.0 g of "PLEX 6631" (acrylic resin from Röhm und Haas, West Germany)
14.0 g of trimethylolpropane triacrylate
14.0 g of neopentylglycolpropane triacrylate
1.16 g of N-methyldiethanolamine.

0.4 g of 3-n-decylthio-5-phenylsulfonylphthalic acid N-methylimide is added as the photoinitiator to 9.6 g of this mixture. The lacquer prepared in this way is applied to glass plates with a 40 μm knife coater. The samples are irradiated with a UV exposure apparatus (Standard Hg-vapour lamp, lamp power: 80 W/cm, distance of lamp: 11 cm, speed of conveyor belt: 50 m/minute). A wipe-resistant film is obtained.

What is claimed is:
1. A Compound of the formula II

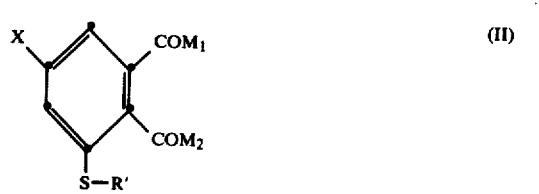

in which $M_1$ and $M_2$ together are —O—, X is —NO$_2$, —OR', —SR' or —SO$_2$R' and the (R')s independently of one another are C$_{1-20}$-alkyl, C$_{3-5}$-alkenyl, C$_{3-5}$-alkynyl, C$_{2-4}$-monohydroxyalkyl, C$_{1-12}$-halogenoalkyl, benzyl, C$_{5-12}$-cycloalkyl, phenyl, carboxyphenyl, halogenophenyl, nitrophenyl, alkyl- or alkoxy-phenyl each having 1-4 C atoms in the alkyl or alkoxy moieties, or acetylaminophenyl.

2. A compound of the formula II according to claim 1, in which $M_1$ and $M_2$ together are —O—, X is —$NO_2$, —Oalkyl having 1-4 C atoms, —$SO_2$-phenyl or SR' and the (R')s independently of one another are $C_{1-10}$-alkyl, $C_{1-10}$-halogenoalkyl, pheny, p-methoxyphenyl, p-toluyl, 2-carboxyphenyl or 5,4-dichlorophenyl.

3. A compound of the formula II according to claim 1, in which $M_1$ and $M_2$ together are —O—, X is —$NO_2$, —$SO_2$-phenyl, —S-phenyl, —S—$C_{1-10}$-alkyl or —S—$C_{1-10}$-halogenoalkyl and R' is $C_{1-10}$-alkyl, $C_{1-10}$-halogenoalkyl, phenyl, p-methoxyphenyl, p-toluyl, 2-carboxyphenyl or 3,4-dichlorophenyl.

4. A compound of the formula II according to claim 1, in which $M_1$ and $M_2$ together are —O—, X is —$NO_2$ and R' is $C_{1-10}$-n-alkyl or phenyl.

* * * * *